United States Patent [19]

Bellinger

[11] 3,999,861
[45] Dec. 28, 1976

[54] FLOW CELL

[75] Inventor: S. Laurence Bellinger, Lake Luzerne, N.Y.

[73] Assignee: Technicon Instruments Corporation, Tarrytown, N.Y.

[22] Filed: June 30, 1975

[21] Appl. No.: 591,683

[52] U.S. Cl. .............................. 356/181; 250/576; 356/246
[51] Int. Cl.² ......................................... G01N 1/10
[58] Field of Search .......... 250/576; 356/181, 244, 356/246, 75

[56] References Cited

UNITED STATES PATENTS

| | | | |
|---|---|---|---|
| 3,080,789 | 3/1963 | Rosin et al. | 356/246 |
| 3,414,354 | 12/1968 | Siegler, Jr. | 356/75 |
| 3,431,424 | 3/1969 | Allen | 356/181 |
| 3,524,066 | 8/1970 | Blakkan | 250/576 |

Primary Examiner—John K. Corbin
Assistant Examiner—F. L. Evans
Attorney, Agent, or Firm—S. P. Tedesco; Stephen E. Rockwell

[57] ABSTRACT

Method and apparatus for photometric analysis of sample fluids for a constituent of interest. There is provided a method of sample analysis comprising the steps of locating the sample fluid in a cell having an axis, directing a ray of light through the sample and the sample-cell interface at an angle to said axis, totally internally reflecting said light ray passed through the interface to be redirected across said sample, and detecting the redirected light ray passed through the sample.

8 Claims, 9 Drawing Figures

FLOW CELL

BACKGROUND OF THE INVENTION

1. Field of the Invention

This invention relates to a flowcell for measurement of fluid sample constituents.

2. Prior Art

Heretofore flowcells for use in continuous-flow analysis have been of the type in which a ray of light is directed transversely through a sample fluid path in a single plane (U.S. Pat. No. 3,518,009) for detection on the opposite side of the path, and of the type such as shown in Bellinger et al U.S. Pat. No. 3,740,158 wherein the sight path is axially along a portion of the fluid path. Commonly, the cross sectional dimension of the fluid path is 1 mm or less which severly limits the cross sectional size of the sight path. In the use of flowcells of the last-mentioned type, a common difficulty has been encountered in the accumulation of debris at the points of the fluid path, coincident with the sight path, where the fluid path enters and leaves the sight path. This debris, which is located where the fluid angularly enters the sight path and leaves it, causes optical noise in sample measurements. Attempts have been made to minimize entrapment of debris, such as small bubbles and dirt, by curving surfaces of the fluid path, as in Isreeli U.S. Pat. No. 3,336,602, or by beveling such surfaces as in Rachlis et al U.S. Pat. No. 3,583,817. Such collection of debris is avoided in Pelavin U.S. Pat. No. 3,418,053 where the fluid path is straight and the light input and output is angled with respect to the path. However, there is a significant light energy loss due to the flowcell structure and such attempts have not been entirely successful. The present invention seeks to obviate these difficulties. Heretofore, as in the last-mentioned structure, attempts have been made to reflect light energy within the flowcell by use of an axially extending silvered or bright surface portion of the cell acting as a mirror reflecting light energy back and forth across the fluid path. However, the significant loss of light energy occassioned by mirror reflections is well known. Further, the length of the sight path is not fixed. Hence, the length of the sight path may be different for different ones of the samples. This gives rise to lack of precision in analysis.

In flowcells, generally, and specifically those utilizing laser illumination, it is old to use total internal reflections for reflection of light energy, such reflections being provided by a polished cell surface. These reflections do not suffer the loss of light energy occassioned by mirror surfaces. The present invention contemplates use of such total internal reflections in a new combination.

Further, attempts are known, as in dye lasers, at multiple pass transverse illumination of a dye path by internal reflections in a dye cell as by Ulrich Fritzler as evidenced in Journal of Physics E: Scientific Instruments, Vol. 7, 1974 printed in Great Britain. However, it is obvious that such attempts were not for the purpose of measurement of a fluid sample constituent and that Fritzler was not faced with the problem of getting light energy out of the cell for detection by a detector.

SUMMARY OF THE INVENTION

One object of the invention is to provide an improved flowcell for photometric determinations of sample fluids for constituents of interest, and wherein entrapment of debris in the form of dirt and small bubbles in the sight path is completely avoided to minimize optical noise. Another object is to provide such a flowcell in which the fluid path is illuminated by light energy making a predetermined number of plural passes through the fluid path from a light input end of the cell to a light output end of the cell. Still another object is to provide in such a flowcell total internal reflections of light across the fluid path, with a light path from the input to the output being characterized in some instances by a zig-zag or spiral configuration. A further object is to provide such a cell which is suitable for use with conventional illumination techniques in the visible and ultra violet wavelength regions and which is well suited, too, for illumination by a laser. There is provided a fluid sample constituent measurement technique comprising the steps of locating the sample fluid in a cell having an axis, directing a ray of light through the sample at an angle to the axis, totally internally reflecting the light ray passed through said sample to be redirected across said sample, and detecting the redirected light ray passed through said sample.

DETAILED DESCRIPTION OF THE PREFERRED EMBODIMENTS

Figure 1:
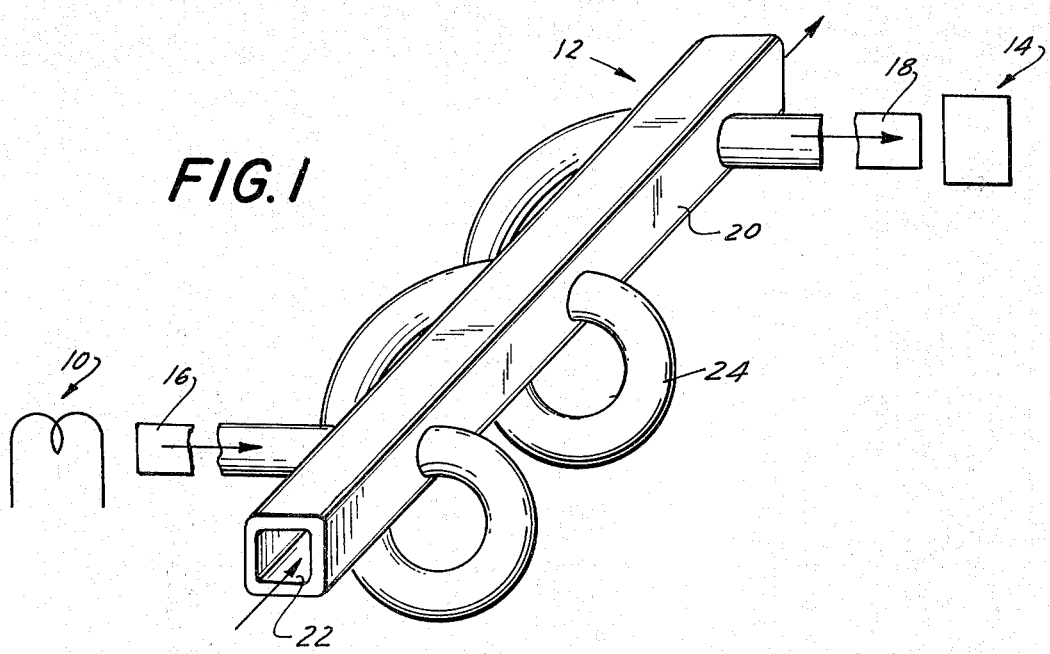
FIG. 1 is a broken isometric view illustrating a photometric system including a flowcell embodying the invention.

In the form of FIG. 1, there is shown a photometric system which includes a light source, indicated generally at 10, a cell or flowcell at 12 and a light detector at 14. The flowcell by way of example is optically coupled in a conventional manner to the light source and the detector by fiber optics 16, 18.

The flowcell 12 comprises an elongated rigid body 20 of inert, transparent material which may be structured of suitable glass quartz or sapphire material. The body 20 may define a longitudinal cylindrical fluid path 22 for the analysis of a constituent of a fluid sample. However, the path is illustrated as being of generally rectangular cross section with inner corners rounded as on a radius as shown. The sample path is adapted to receive in a conventional manner (Smythe and Shamos U.S. Pat. No. 3,804,593) a stream of liquid samples seriatum each isolated from its neighbor by a gas segment, and such gas may conform more readily to the cross section of the path having rounded corners than without such rounded corners. The generally rectangular cross section of the fluid path obviates the lense effect which is present in a path defining a cylindrical surface through which light is passed transversely as in the present invention.

Figure 2:
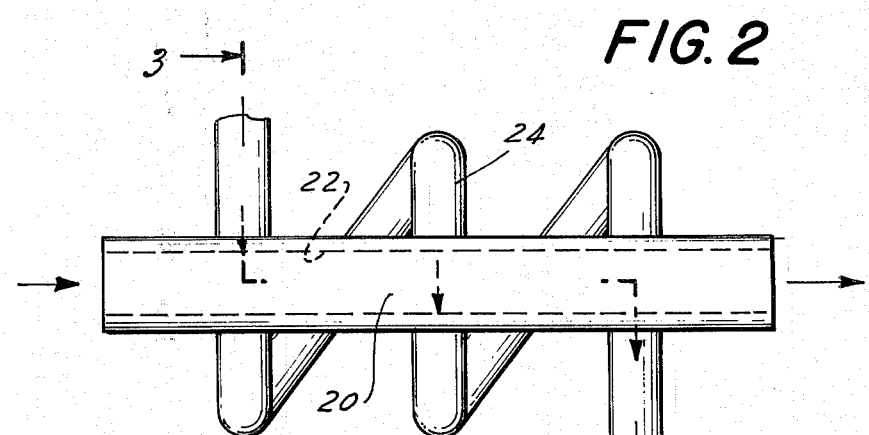
FIG. 2 is a top plan view of the cell; omitting the light source and the detector.
Figure 3:
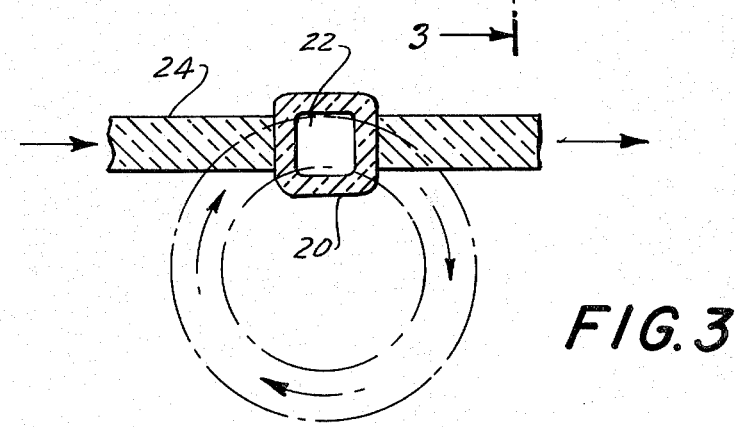
FIG. 3 is a section view taken on line 3—3 of FIG. 2.

For ease of manufacture, two opposite facing sides of the body 20 are flat to coact with the means to be described hereinafter for totally internally reflecting the light from the source 10 across the light path a number of times and which in this form includes a structure 24 which is generally of coil shape having a light input and a light output at opposite ends of the coil forming a solid rod. The coil or spiral 24 is interrupted by the body 20 and is structured of suitable material having a relatively high refractive index for light piping such as glass or quartz, but is preferably formed of sapphire material. Each turn of the coil or spiral 24 has two flat surfaces in registry with one another as shown in FIG. 2 and secured, as with optical cement, to the lastmentioned flat surfaces of the body 20. As shown, the body may have a rectangular cross section which is square. As shown in the last-mentioned view, each turn of the spiral 24 is structured so that on the next pass of light from the preceding pass, said next pass is in a location across a portion of the fluid path 22 nearer one end thereof. The light pipe forming the spiral 24, in which light is totally internally reflected, has a cross-sectional dimension approaching the cross section size of the fluid path 22 as shown. If the spiral light pipe 24 makes three passes of light across the fluid path 22 as shown, and the fluid path 22 has a cross-sectional dimension of 1 mm, the effective light path of the cell is essentially 3 mm.

The sensitivity of the flowcell increases with the number of light passes across the fluid path. However, the light loss increases by light divergence as the number of light passes across the flow path 22 increases. It is to be understood that the number of light passes illustrated across the light path 22 is for the purpose of example only. If desired, the spiral 24 may be jacketed (not shown) and/or the body 20 may be provided with a light shield, not shown, to shield the fluid path 22 from ambient light external to the body 20. One advantage of the flowcell is that it has a known optical length which does not differ from sample to sample. In practice, each turn of the spiral 24 where it is to be cemented by optical cement to the body 20 is highly polished as is the surface of the body 20 to which it is cemented.

Figure 4:
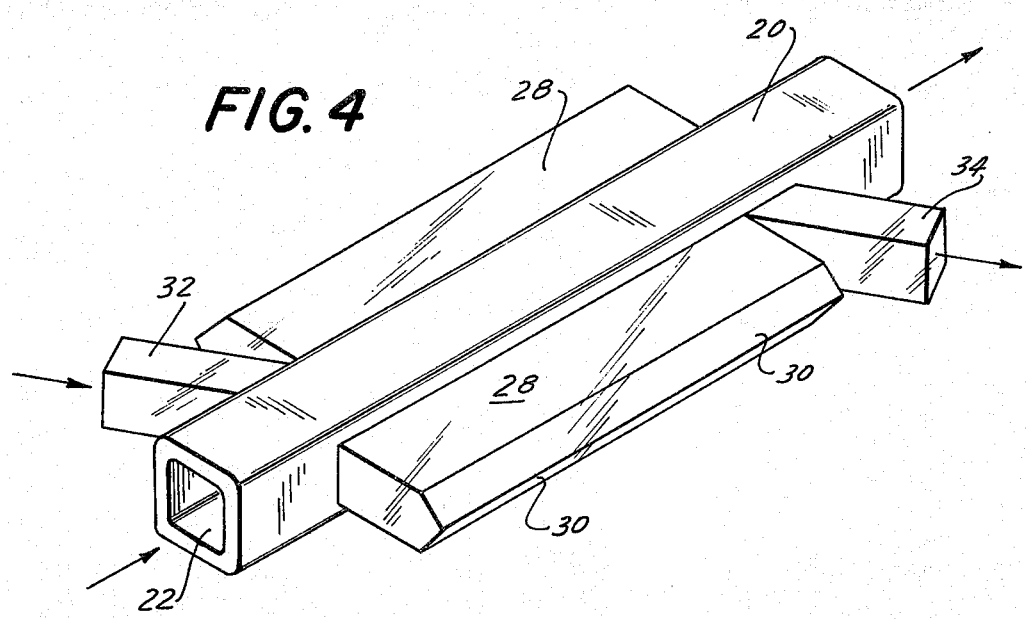
FIG. 4 is a view similar to FIG. 1 but omitting the light source and the detector and illustrating a modified form of the flowcell.
Figure 5:
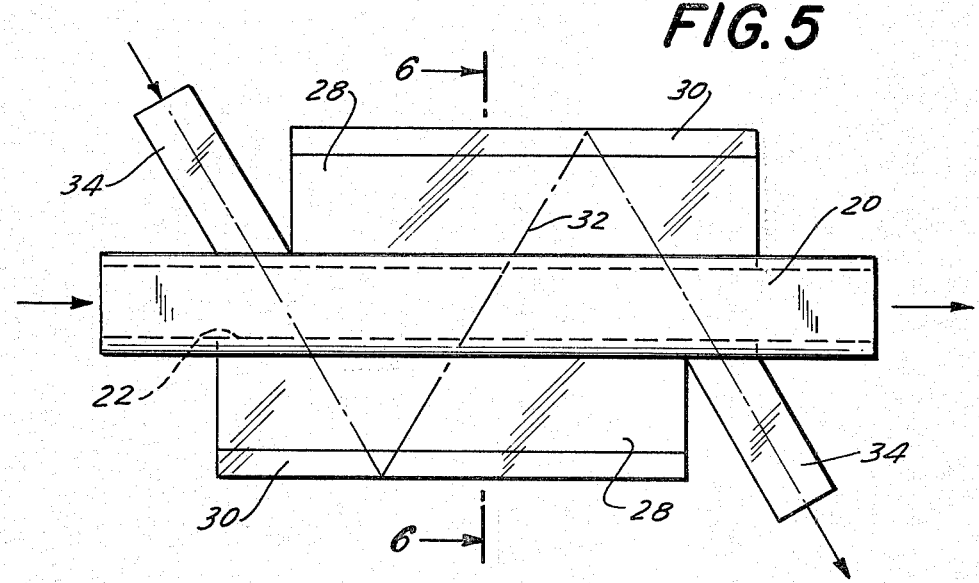
FIG. 5 is a view similar to FIG. 2 and illustrating the form of FIG. 4.
Figure 6:
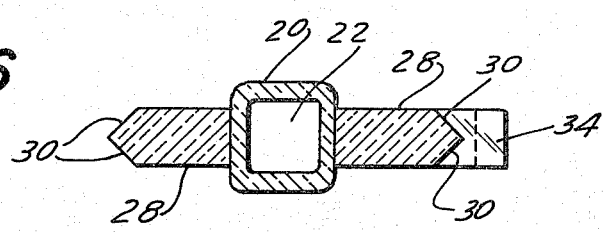
FIG. 6 is a cross sectional view taken on line 6—6 of FIG. 5.

In the modified form of the flowcell shown in FIGS. 4–6, the body of the flowcell is illustrated as being identical to that of the form of FIG. 1 and like reference numerals designate like parts. In this form, a means for directing light back and forth across the flow path 22 includes fin members 28 structured of glass, quartz or sapphire material and essentially flat. All surfaces of the members 28 are highly polished, and each fin member has a base which is secured to a highly polished surface portion of the body 20 by optical cement in axial offset relationship as illustrated in FIG. 5. The outer side edge portion of each fin member 28 is formed by a pair of adjoining reflectant flat edges 30 meeting one another at a 90° angle which point of meeting lies in the median plane of the fin member. In the illustrated form, each fin member 28 is elongated axially of the body 20. The width of the fin members may vary depending upon the number of light passes across the flow path 22 as will appear more readily hereinafter.

In the form of FIG. 4, the flowcell has a light pipe input 32 and a light pipe output 34 at the respective end portions of the flowcell. The light input 32 and the output 34 are angled with reference to the body 20 so as to define an acute angle therewith which angle is the same for each. The angle is shown as being approximately 30° for the purpose of example. The inner end of each of these members 32, 34 is highly polished and secured to a similarly polished surface portion of the body 20 by optical cement. The members 32, 34 are shown as being identical. As shown in FIG. 5, the light input 32 and the light output 34 are so constructed and arranged relatively to the fin members 28, that the light traverses the fluid path 22 diagonally thereof three times before exiting through the output 34. Light directed across the fluid path 22 by the input 32 is totally internally reflected back across the fluid path 22 by one of the fin members 28 in the manner shown in FIG. 5. As illustrated, it is directed across the fluid path once by said member 28. Similarly, the light reflected across the fluid path 22 by the last-mentioned fin member 28 is reflected back across the fluid path in a direction toward the light output 34 by the other fin member 28. During this reflecting of the light back and forth across the fluid path 22, the light energy entering the respective fin member 28 is essentially contained therein by total internal reflection at the flat surfaces of the fin members 28 which minimizes loss of light energy by divergence of such energy.

Figure 7:
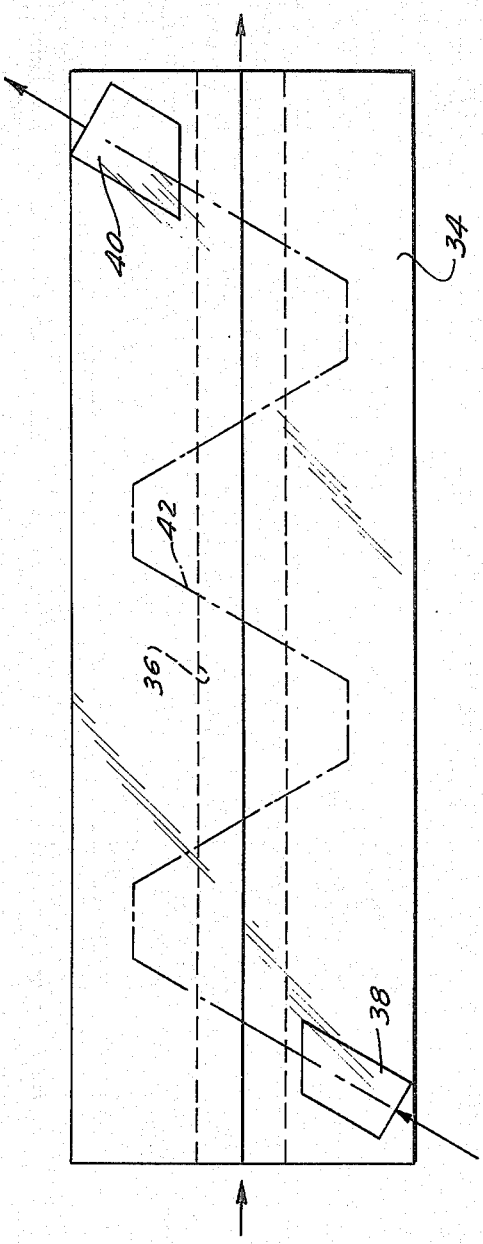
FIG. 7 is a top plan view illustrating a further modification of the flowcell of the invention.
Figure 8:
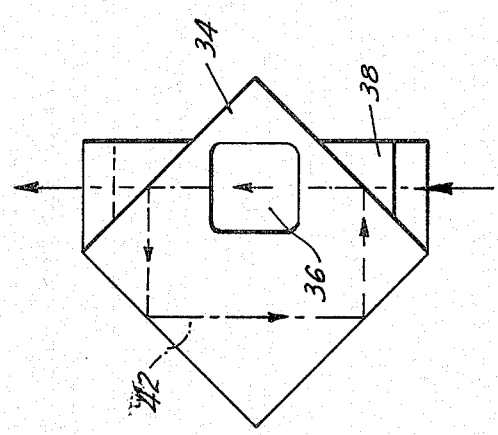
FIG. 8 is an end view of the flowcell of FIG. 7.
Figure 9:
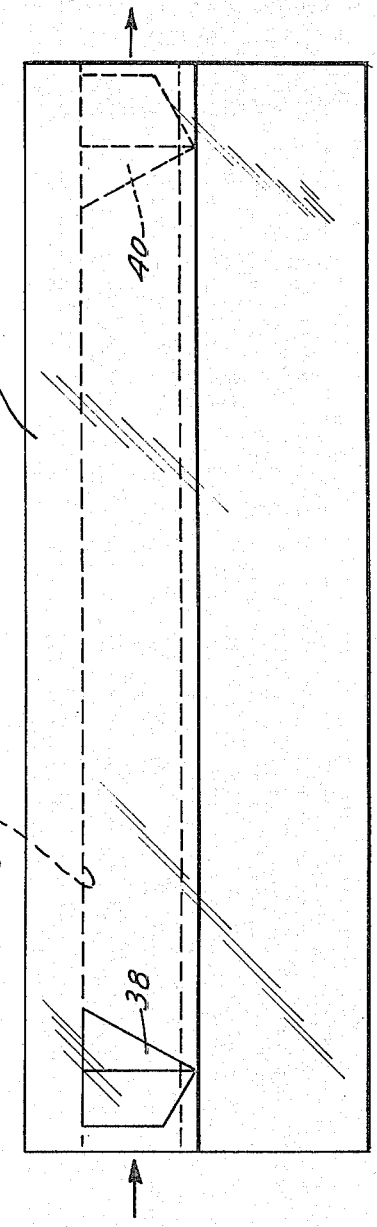
FIG. 9 is a side elevational view of the flowcell of FIG. 7.

The modified form of the invention shown in FIGS. 7–9 is less optically efficient than the forms of FIGS. 1 and 4 with ordinary types of illumination such as a tungsten filiment lamp or an arc lamp due to losses of light by divergence of light energy. However the flowcell of FIG. 7 is extremely efficient with a source of illumination such as a nonillustrated laser. In this form the body 34 of the flowcell is of rectangular cross section and, more specifically, square cross section. The body is elongated and may be structured of glass, quartz or sapphire material and defines a longitudinal, straight fluid path 36 having an inlet end and an outlet end. The fluid path 36 may be cast in glass or quartz material of the body by the use of conventional sacrificial tube techniques. The path 36 is dimensioned and shaped similarly to the path 22 previously described and is located in one half of the body as illustrated in FIG. 8. All external surfaces of the body 34 are highly polished in a manner similar to the form of FIG. 4. The form of FIG. 7 has light pipe input and output members 38 and 40 respectively which are angled with respect to the body and the flow path in the manner indicated in FIGS. 7 and 8 of the drawings for example. The construction and arrangement of the optical parts previously described is such that light inputted through the member 38 makes three diagonal passes through the fluid path 36 before exiting through the outlet 40, the light path being indicated at 42. The member 40 defines a light output of larger area than the input 38 to allow the light energy to exist from the flowcell through such light in its passage across the fluid path 36 and the liquid contained therein is refracted somewhat, depending on the particular index of refraction of the fluid in the path 36. The light path defines a spiral of flattened form as shown. The flattened spiral form of the light path 42 is produced from the four sides of the body 34 which totally internally reflect the light ray inputted into the body prior to its output in the aforesaid manner. As previously indicated, such internal reflection is more efficient than mirror-surface reflection. Using the form of FIG. 7 as an example for comparison purposes, if mirrors were used in the form of FIG. 7 as substitutes for the four sides of the body 34 which reflect light internally, assuming a 85% reflection at each surface, the mirror configuration would have an efficiency of light reflection of 23% of the light energy as opposed to 100% efficiency of reflection of light in the form of FIG. 7.

While several forms of the flowcell have been illustrated it will be apparent, especially to those versed in the art, that the flowcell may take other forms and is susceptible to various changes without departing from the principles of the invention.

What is claimed is:

1. A method for photometric quantitation of a constitutent of a fluid sample in an elongated cell having an axis, comprising the steps of: flowing the sample through a longitudinal fluid path in the cell, directing a ray of light at an angle to said axis and proximate one end of said path through said sample in said path and then through an interface of said sample and said cell, totally internally reflecting said light ray passed through said interface to redirect said ray across said sample in a different axial location, continuing to totally internally reflect said ray across said sample to an output of said ray proximate to the other end of said path and at an angle to said axis, while determining the number of passes of said ray through said sample, and detecting the absorbance of said ray by said sample from said ray output.

2. A method as defined in 1, wherein: said continuing to totally internally reflect said ray across said sample to said ray output is in spiral form.

3. Apparatus for photometric quantitation of a constituent of a fluid sample, comprising: a light source; elongated transparent means having an axis and defining a longitudinal sample flow path having an inlet and an outlet; means directing at an angle to said axis and proximate to one end of said flow path a light ray from said source through said sample and then through an interface of said sample with said means defining said flow path; means beyond said interface totally internally reflecting said ray and redirecting said ray across said sample in a different axial location; said ray redirecting means continuing to totally internally reflect said ray across said sample a predetermined number of times to an output of said ray at an angle to said axis proximate to the other end of said path; and means detecting the absorbance of said ray by said sample from said ray output.

4. Apparatus as defined in claim 3, wherein: said means defining said flow path is substantially flat in the area where said ray is redirected across said sample.

5. Apparatus as defined in claim 3, wherein: said means continuing to totally internally reflect said ray across said sample a predetermined number of times to said ray output is in axially interrupted spiral form.

6. Apparatus as defined in claim 3, wherein said means continuing to totally internally reflect said ray across said sample to said ray output comprises a light pipe substantially in the form of a spiral which is interrupted by said means defining said flow path.

7. Apparatus as defined in claim 6 wherein: the turns of said spiral are fixed to said means defining said flow path.

8. Apparatus as defined in claim 3, wherein: said means continuing to totally internally reflect said ray across said sample to said ray output comprises a pair of fin members fixed to opposite sides of said means defining said flow path.

* * * * *